United States Patent [19]

Hartman

[11] 4,021,438
[45] May 3, 1977

[54] NOVEL PROCESS FOR THE PREPARATION OF THIAZOLES

[75] Inventor: George D. Hartman, Plainsboro, N.J.

[73] Assignee: Merck & Co., Inc., Rahway, N.J.

[22] Filed: Oct. 22, 1975

[21] Appl. No.: 624,796

[52] U.S. Cl. .................. 260/302 R; 260/455 R; 260/465 B
[51] Int. Cl.² ............. C07D 277/38; C07D 277/34
[58] Field of Search ............................. 260/302 R

[56] References Cited
OTHER PUBLICATIONS

Oldenziel et al., *Tetrahedron Letters*, 2777–2778 (1972).

*Primary Examiner*—R. J. Gallagher
*Attorney, Agent, or Firm*—David L. Rose; J. Jerome Behan

[57] ABSTRACT

A novel process disclosed for the preparation of substituted thiazoles. The process utilizes a loweralkyl thioformate or a substituted loweralkyl thioformate and an isocyanoacetonitrile or an isocyanoloweralkanoate in the presence of a base.

9 Claims, No Drawings

NOVEL PROCESS FOR THE PREPARATION OF THIAZOLES

DESCRIPTION OF THE PRIOR ART

Thiazoles have been of chemical industrial importance for a considerable period of time as chemical intermediates. In particular 4-cyano thiazole is employed as an intermediate in the preparation of 2-(-thiazoly) benzimidazole and 5-isopropoxycarbonylamino -2-(4-thiazolyl) benzimidazole. These compounds are important biologically active compounds and are widely employed for the treatment of parasitic infections in man and animals.

Prior art preparations of substituted thiazoles have involved condensations of isocyanides with dithioates. In Tetrahedron Letters 2777 (1972) a preparation of aryl thiazoles is described in which p-toluene sulfonyl methyl isocyanide is condensed with an aryl carboxymethyl dithioate. The instant process utilizes a substituted loweralkyl thioformate and the foregoing reference states that such monothiocarboxylates afforded no reaction. Thus, the instant invention yields results which are not taught by the prior art and are in fact totally unexpected results since the prior art indicated negative results for the reagent used in this process.

SUMMARY OF THE INVENTION

The instant application discloses a novel process for the preparation of substituted thiazole compounds. In particular said process prepares the substituted thiazole compounds from substituted lower alkylthioalkanoates and an isocyanoacetonitrile or an isocyanoloweralkanoate. Thus, it is an object of this invention to describe such thiazole compounds and the compounds utilized in said process. It is a further object of this invention to describe the reaction conditions for the efficient production of such compounds. Further objects will become apparent from the following Description of the Invention.

DESCRIPTION OF THE INVENTION

The substituted thiazoles of this invention are prepared according to the following reaction scheme:

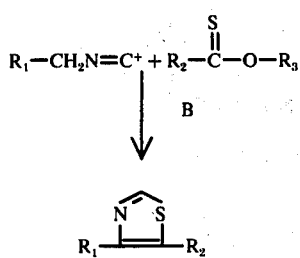

wherein $R_1$ is cyano or loweralkoxycarbonyl; $R_2$ is hydrogen, loweralkyl or phenyl; $R_3$ is loweralkyl or phenyl; and B is a base.

The representation of the substituted isonitrile as $R_1-N\equiv C^{\ominus}$ is recongized by those skilled in this art as depicting a carbene in which one of the two unbonded orbitals of the carbon atom contains an electron pair and the other has no electron pair. The carbene is often represented also as:

In the instant application the term "lower" as used in "loweralkyl" or "loweralkoxy" refers to those alkyl or alkoxy groups which contain from 1 to 5 carbon atoms in either a straight or branched chain. Exemplary are methyl, ethyl, propyl, isopropyl, butyl, tert-butyl, pentyl,methoxy ethoxy, propoxy, isopropoxy, butoxy, sec. butoxy, pentoxy, and the like.

In the foregoing process the $R_1$ substituted isonitrile is combined with an $R_2$ substituted loweralkyl thioformate in a polar, protic solvent. Preferred solvents are loweralkanols such as methanol, ethanol, propanol, isopropanol, and the like. Ethanol is the most preferred solvent. The combined reagents are then added to a base in the same solvent. The initial combination of the reagents with the base is occasionally exothermic and external cooling may be necessary. The initial temperature is from 0° to 20° C. Following the addition the temperature of the reaction mixture is raised to from 20° C. to the reflux temperature of the reaction mixture or to 100° C. for from ½ hour to 3 days. Generally the reaction is complete at from 40° to 60° C. in from 1 to 3 hours.

Generally equimolar quantities of the isonitrile and thioformate reagent are employed. It has been found that using an excess of one reagent over the other offers no benefit or detriment to the process. Since such excess reagent must be removed at the completion of the reaction, it is preferred to employ equimolar quantitites.

The B in the foregoing reaction scheme is a base. It has been found that, while any base will produce the thiazole, bases such as an alkali metal cyanide, particularly sodium cyanide; ammonium cyanide; an alkali metal alkoxide, preferably sodium alkoxide are preferred. Other inorganic bases such as alkali metal and alkaline earth metal hydroxides, may also be employed. The most preferred base has been found to be sodium cyanide.

The base is generally required in only catalytic amounts although higher amounts of base have not been found to be detrimental to the reaction. Thus, it is not necessary to provide an excess of base or even to provide strongly basic conditions. Catalytic amount of weak bases such as alkali metal cyanides are sufficient to catalize the reaction.

The $R_3$ group is, along with the oxygen attached, merely a leaving group and does not form part of the final product. Of the loweralkoxy and phenoxy leaving groups ($R_3$=loweralkyl and phenyl respectively) the preferred leaving group is ethoxy ($R_3$=ethyl).

The preferred compounds prepared by the process of this invention are those wherein $R_1$ is cyano and $R_2$ is hydrogen.

The substituted loweralkylthioformate and isocyanoacetonitrile reagents are generally known in the art, or processes for their preparation readily available to those skilled in this art.

The isocyanoacetonitrile or isocyanoloweralkanoate reagents are generally prepared by reacting an appropriately substituted $R_1$-$CH_2NHCHO$ reagent with phosphorous oxychloride in the presence of a base such as triethylamine. The reaction is run at from -50° to 0° C. and the isocyanoacetonitrile kept cold and used as soon as it is prepared.

The substituted loweralkylthioformates are prepared from corresponding ortho ester as described in Tetrahedron Letters 17 pg. 2083 (1968). Generally the procedure involves treatment of an appropriate ortho ester with gaseous hydrogen sulfide in the presence of a catalytic amount of a Lewis Acid. A solvent is optional however, it is generally preferred to conduct the reaction in the absence of a solvent. The reaction is generally conducted at from -10° to 30° C. The lower molecular weight substituents generally require lower temperatures. The preferred Lewis Acid catalysts are zinc chloride and ferric chloride. The reaction is generally complete in from ½ hour to 3 days.

The following examples will illustrate the preferred embodiments of the instant invention. However, such examples should be construed as limitative of the scope of this invention.

EXAMPLE 1

To a mixture of 10.0 g. (0.119 m) of N-formylaminoacetonitrile, 21.8 g. (0.215 m) of triethylamine, and 10 ml. of methylene chloride at -25° C. is added dropwise 18.1 g. (0.11 m) of phosphorous oxychloride over 10 minutes. After stirring another 10 minutes, the reaction mixture is yellow in color. This solution is allowed to warm to 0° C., suction filtered, extracted once with a solution of 28.4 g. sodium carbonate in 120 ml. water, and then twice with water. The solution is then dried over magnesium sulfate, filtered, and the solvent removed in vacuo at 0°–10° C. The resulting isocyanoacetonitrile, recovered as an oil, is taken up in absolute ethanol, 11.0 g. (0.120 m) of 0-ethyl thioformate is added, and the resulting solution added dropwise to a suspension of 1.5 g. of sodium cyanide in 200 ml. of absolute ethanol. After stirring for 20 hours at ambient temperature, the solvent is stripped on the rotary evaporator and the residue is extracted several times with hot hexane to afford a 23% yield of 4-cyanothiazole.

EXAMPLE 2

A solution of 4.52 g. (0.04 m) of ethyl isocyanoacetate and 3.60 g. (0.04 m) of ethyl thioformate in 15 ml. of absolute ethanol is added dropwise with vigorous stirring to a suspension of 0.25 g. of sodium cyanide in 10 ml. ethanol at 15° C. An exotherm developes during the addition and is moderated with ice-bath cooling. The reaction mixture is warmed at 50° C. for 30 minutes. The solvent is then removed in vacuo and the resulting residue extracted with several portions of hot hexane to give a 92% yield of 4-ethoxycarbonyl thiazole.

EXAMPLE 3

A solution of 2.25 g. (0.02 m) of ethyl isocyanoacetate and 2.08 g. (0.02 m) 0-ehtyl thioacetate in 10 ml. absolute ethanol is added dropwise to a suspension of 0.25 g. sodium cyanide in 10 ml. absolute ethanol. After 5 minutes a mild exotherm occurs and the temperature rises to from 22° to 32° C. remaining there for about ½ hour. The reaction mixture is then heated at 50° c. for 8 hours at which time the smell of isonitrile is gone. The reaction mixture is then evaporated to dryness in vacuo leaving a dark oil which is extracted several times with hot hexane. The hexane is evaporated affording 2.8 g. (82%) of a tan solid which is the desired 4-ethoxycarbonyl-5-methylthiazole. This solid is recrystallized from ether/hexane affording a pure product with a m.p. 89°–90° C. Following the foregoing procedures employing 0-ethyl thiobutyrate in place of 0-ethyl thioacetate, there is obtained 4-ethoxycarbonyl-5-(n-propyl) thiazole with a boiling point of 85°–87° C. at 0.15 mm of Hg.

EXAMPLE 4

0-ethylthiobenzoate is prepared from triethylorthobenzoate in 70% yield by the procedure of A. Ohns, et al *Tetrahedron Letters* 17, 2083 (1968).

A solution of 2.26 g. (0.02 m) of ethylisocyanoacetate and 3.33 g. (0.02 m) of 0-ethylthiobenzoate in 10 ml. ethanol is added to a vigorously stirred suspension of 0.2 g. of sodium cyanide in 10 ml. of ethanol. The resulting mixture is then heated at 50° C. for 20 hours. The blackened solution is then evaporated to dryness affording a tar which is chromatographed on silica gel eluting with chloroform to afford 1.0 g. (22%) of the desired 4-ethoxycarbonyl- 5-phenyl thiazole.

What is claimed is:

1. A process for the preparation of a compound having the formula:

wherein $R_1$ is cyano or loweralkoxycarbonyl, and $R_2$ is hydrogen, loweralkyl or phenyl, which comprises combining at from 0° to 20° C in a polar, protic solvent, a compound having the formula:

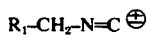

with a compound having the formula:

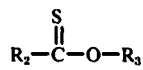

wherein $R_1$ and $R_2$ are as previously defined and $R_3$ is loweralkyl or phenyl in the presence of a base, and then raising the temperature to from 20° C to the reflux temperature or to 100° C for from ½ hour to 3 days.

2. The process of claim 1 wherein the base is an alkali metal or ammonium cyanide, an alkali metal alkoxide, an alkali metal or alkaline earth metal hydroxide.

3. The process of claim 2 where the base is sodium cyanide or a sodium alkoxide.

4. The process of claim 3 wherein the base is sodium cyanide.

5. The process of claim 1 in which the compounds are reacted at from 40° to 60° C. for from 1 to 3 hours.

6. The process of claim 1 wherein $R_3$ is loweralkyl.

7. The process of claim 1 wherein $R_3$ is ethyl.

8. The process of claim 1 wherein $R_1$ is cyano and $R_2$ is hydrogen.

9. The process of claim 1 wherein $R_1$ is loweralkoxycarbonyl and $R_2$ is loweralkyl.

* * * * *